United States Patent [19]

Kalopissis et al.

[11] 4,093,640

[45] June 6, 1978

[54] DOUBLE SALT OF ZINC CHLORIDE AND INDAMINES

[75] Inventors: Gregoire Kalopissis, Paris; Andree Bugaut, Boulogne-sur-Seine; Francoise Estradier, Paris, all of France

[73] Assignee: L'Oreal, Paris, France

[21] Appl. No.: 699,207

[22] Filed: Jun. 23, 1976

Related U.S. Application Data

[60] Division of Ser. No. 553,067, Feb. 25, 1975, Pat. No. 3,984,443, which is a division of Ser. No. 387,613, Aug. 13, 1973, Pat. No. 3,876,368, and a continuation-in-part of Ser. No. 180,455, Sep. 14, 1971, abandoned.

[30] Foreign Application Priority Data

Sep. 18, 1970 France ............................... 70.34041

[51] Int. Cl.$^2$ ............................................. C07F 3/06

[52] U.S. Cl. ............................ 260/429.9; 260/270 H; 260/293.64; 260/293.79; 260/293.85; 260/293.86

[58] Field of Search ....................................... 260/429.9

[56] References Cited

U.S. PATENT DOCUMENTS

| | | | |
|---|---|---|---|
| 1,867,962 | 7/1932 | Allchin | 260/429.9 |
| 2,052,424 | 8/1936 | Sexton | 260/429.9 X |
| 2,370,339 | 2/1945 | Wirth et al. | 260/429.9 X |
| 2,686,798 | 8/1954 | Gmitter | 260/429.9 |
| 3,052,705 | 9/1962 | Brasen et al. | 260/429.9 X |

*Primary Examiner*—Helen M. S. Sneed
*Attorney, Agent, or Firm*—Cushman, Darby & Cushman

[57] ABSTRACT

Indamine having the formula

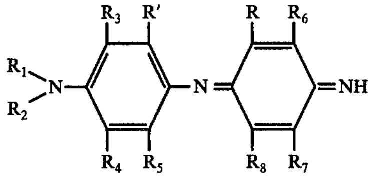

wherein R and R' each independently represent a member selected from the group consisting of hydrogen, lower alkyl having 1–4 carbon atoms, lower alkoxy having 1–4 carbon atoms, amino, acylamino wherein the acyl moiety has 1 to 4 carbon atoms and hydroxy, with the proviso that one, but not both of R and R' is said amino, acylamino or hydroxy; $R_1$ and $R_2$ each independently represent a member selected from the group consisting of lower alkyl having 1–4 carbon atoms and lower alkyl having 1–4 carbon atoms and substituted with a member selected from the group consisting of hydroxy, acylamino wherein the acyl moiety has 1 to 4 carbon atoms, carbamyl, piperidino, benzoylamino and alkylsulfonamido wherein the alkyl moiety has 1 to 4 carbon atoms; $R_3$, $R_4$, $R_5$, $R_6$, $R_7$ and $R_8$ each independently represent a member selected from the group consisting of hydrogen, lower alkyl having 1–4 carbon atoms and lower alkoxy having 1–4 carbon atoms, and the salts formed by these indamines with organic or inorganic acids, in particular, their acetates, hydrochlorides, hydrobromides, persulfates, perchlorates and the double zinc salts of these compounds, which can, of course, be in a tautomeric form of that represented by formula (I), are usefully employed for dyeing keratinous fibers, and, in particular, human hair.

1 Claim, No Drawings

DOUBLE SALT OF ZINC CHLORIDE AND INDAMINES

This is a division of application Ser. No. 553,067 filed Feb. 25, 1975 now U.S. Pat. No. 3,984,443 which is a division of Ser. No. 387,613 filed Aug. 13, 1973, now U.S. Pat. No. 3,876,368 which is a CIP of Ser. No. 180,455 filed Sept. 14, 1971 now abandoned.

The present invention relates to novel indamines having the formula:

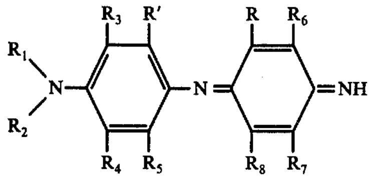

(I)

wherin R and R' each independently represent a member selected from the group consisting of hydrogen, lower alkyl having 1–4 carbon atoms, lower alkoxy having 1–4 carbon atoms, amino, acylamino wherein the acyl moiety has 1 to 4 carbon atoms, amino, acylamino wherein the acyl moiety has 1 to 4 carbon atoms and hydroxy with the proviso that one, but not both of R and R' is said amino, acylamino or hydroxy; $R_1$ and $R_2$ each independently represent a member selected from the group consisting of lower alkyl having 1–4 carbon atoms and lower alkyl having 1–4 carbon atoms and substituted with a member selected from the group consisting of hydroxy, amino acylamino wherein the acyl moiety has 1 to 4 carbon atoms, carbamyl, piperidino, benzoylamino and alkylsulfonamido wherein the alkyl moiety has 1 to 4 carbon atoms; $R_3$, $R_4$, $R_5$, $R_6$, $R_7$ and $R_8$ each independently represent a member selected from the group consisting of hydrogen, lower alkyl having 1–4 carbon atoms and lower alkoxy having 1–4 carbon atoms and to the salts formed by these indamines with organic or inorganic acids, in particular, their acetates, hydrochlorides, hydrobromides, persulfates, perchlorates and the double zinc salts of these compounds, which can, of course, be in a tautomeric form of that represented by formula (I).

For instance, a tautomeric form of the indamine of formula (I) can be:

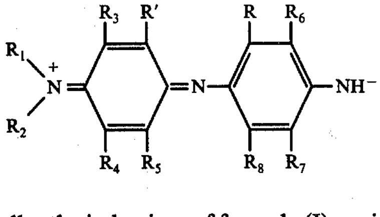

Generally, the indamines of formula (I) are isolated in the form of their salts, these latter generally being more easy to obtain because of their solubility characteristics.

The indamines or indamine salts of formula (I) can be prepared by condensing a paraphenylene diamine having the formula:

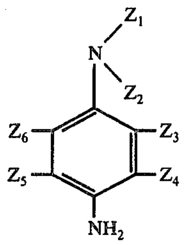

(II)

wherein $Z_1$ and $Z_2$ both represent hydrogen or both represent a member selected from the group consisting of lower alkyl having 1–4 carbon atoms and lower alkyl having 1–4 carbon atoms and substituted with a member selected from the group consisting of hydroxy, acylamino wherein the acyl moiety has 1 to 4 carbon atoms, carbamyl, piperidino, benzoylamino and alkylsulfonamido wherein the alkyl moiety has 1 to 4 carbon atoms, and $Z_3$, $Z_4$, $Z_5$ and $Z_6$ each independently represent a member selected from the group consisting of hydrogen, lower alkyl having 1–4 carbon atoms and lower alkoxy having 1–4 carbon atoms, on a compound having the formula:

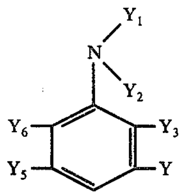

(III)

wherein Y represents a member selected from the group consisting of amino, acylamino wherein the acyl moiety has 1 to 4 carbon atoms and hydroxy; $Y_1$ and $Y_2$ both represent hydrogen when $Z_1$ and $Z_2$ are other than hydrogen, or both represent a member selected from the group consisting of lower alkyl having 1–4 carbon atoms and lower alkyl having 1–4 carbon atoms and substituted with a member selected from the group consisting of hydroxy, acylamino wherein the acyl moiety has 1 to 4 carbon atoms, carbamyl, piperidino, benzoylamino and alkylsulfonamido wherein the alkyl moiety has 1 to 4 carbon atoms when $Z_1$ and $Z_2$ are both hydrogen; $Y_3$, $Y_4$ and $Y_5$ each independently represent a member selected from the group consisting of hydrogen, lower alkyl having 1–4 carbon atoms and lower alkoxy having 1–4 carbon atoms. The condensation reaction is carried out in an aqueous alkaline medium, an aqueous acetonic alkaline medium or in an aqueous isopropanol alkaline solution, in the presence of an oxidizing agent. The initial reactants, represented by formulae II and III above can be used in the form of one of their salts. If necessary or desirable, the resulting indamine or indamine salt can be further transformed into the desired indamine salt.

The oxidizing agent used in the above condensation reaction is advantageously hydrogen peroxide or a water soluble inorganic peroxy salt such as an alkaline persulfate including ammonium persulfate, the use of which facilitates the isolation of the indamine of formula I in the form of an insoluble persulfate.

When the oxidizing agent used is hydrogen peroxide and it is desired to obtain an indamine salt that is relatively insoluble in water, the above condensation reaction can be followed by addition to the reaction mixture either of an acid corresponding to the desired salt, or of a salt of that acid which is more soluble in water than the desired indamine salt, for example, ammonium persulfate.

It has further been noted that even when it is desired to prepare an indamine persulfate, it is often advantageous to proceed in two stages, the first stage comprising carrying out the condensation in the presence of hydrogen peroxide and the second stage comprising adding an alkaline persulfate, including ammonium persulfate, to the reaction mixture.

When it is desired to obtain indamine salts which are very soluble in water, it is necessary to produce these salts in a two-stage operation. In the first stage, there is prepared an indamine salt, such as a persulfate or a hydrochloride, which is relatively insoluble and, therefore, can be isolated. In the second stage, this salt is treated with an alkaline solution from which the indamine of formula I can be extracted with a suitable solvent such as chloroform or methylisobutyl ketone. This indamine can then be changed into the desired salt by the addition of the corresponding acid to the solvent phase. This way of operating is particularly applicable when it is desired to prepare an acetate of the indamine.

When it is desired to obtain a indamine of formula (I), which is not salified and which is insoluble in water, the condensation reaction is preferably performed in the presence of hydrogen peroxide and the resulting indamine is separated from the reaction medium by any suitable technique, for example, by filtering.

On the other hand, when it is desired to obtain an indamine of formula (I) which is so soluble in water that its direct isolation from the reaction medium is not feasible, the indamine, after being prepared by the above condensation reaction in the presence of hydrogen peroxide, is converted, in a first stage, into a water insoluble salt thereof, such as its persulfate or its hydrochloride, by operating in the way described above. The salt thus formed is isolated as by filtering, for instance, and then in a second stage is treated with a concentrated alkaline solution, operating in a minimum of water. Finally, if necessary or desirable, the indamine is extracted with a suitable solvent such as chloroform or methylisobutyl ketone.

To obtain double salts of zinc and the indamine of formula (I), it suffices to add an aqueous solution of a suitable zinc salt to an aqueous solution of a soluble indamine salt.

Representative paraphenylenediamines of formula (II) that can be used in accordance with the present invention are, for example, paraphenylenediamine, paratoluylenediamine, 2,5-diamino anisole, 2-methoxy 5-methyl paraphenylenediamine, 2,6-dimethyl 3-methoxy paraphenylenediamine, 1,4-diamino durene, N,N-diethyl paraphenylenediamine, N,N-dimethyl paraphenylenediamine and N,N-(ethyl, β-mesylaminoethyl) 4-amino 3-methyl aniline.

Compounds representative of those having formula (III) above include, for instance 2,4-diamino anisole, 3-amino 4-methyl acetanilide, 3-amino acetanilide, N,N-dimethyl metaphenylenediamine, meta (N,N-dimethyl) amino acetanilide and N,N-diethyl metaaminophenol.

The condensation reaction is generally carried out at atmospheric pressure and at a temperature ranging from about −10° C to 30° C. Generally, the paraphenylene diamine and the compound represented by formula III are employed in essentially equimolar amounts. When the reaction medium is an aqueous alkaline solution, an alkalinizing agent such as ammonia or the like is present in amounts such that the pH is about 8 to 11. When the reaction medium is an aqueous acetonic solution, acetone can comprise between about 20 to 70 weight percent of the medium. When the reaction medium is an aqueous isopropanol solution, isopropanol can comprise between about 20 to 50 weight percent of the medium. The oxidizing agent is generally present in stoichiometric amounts when this oxidizing agent is a persalt, and in excess when it is hydrogen peroxide.

The indamines of formula (I) can also be prepared by condensing a benzoquinonediimine having the formula:

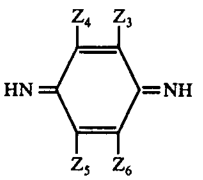

(IV)

wherein $Z_3$, $Z_4$, $Z_5$ and $Z_6$ each represent a member selected from the group consisting of hydrogen, lower alkyl having 1–4 carbon atoms and alkoxy radicals having 1–4 carbon atoms with the proviso that at least two of $Z_3$, $Z_4$, $Z_5$ and $Z_6$ do not represent hydrogen, on a compound of formula (III) above wherein Y, $Y_3$, $Y_4$ and $Y_5$ have the meaning given above and $Y_1$ and $Y_2$ each represent a member selected from the group consisting of lower alkyl having 1–4 carbon atoms and lower alkyl having 1–4 carbon atoms and substituted by a member selected from the group consisting of hydroxy, acylamino wherein the acyl moiety has 1 to 4 carbon atoms, carbamyl, piperidino, benzoylamino and alkylsulfonamido wherein the alkyl moiety has 1 to 4 carbon atoms.

This condensation is carried out either in an aqueous medium which, if desired, can contain a salt of an acid corresponding to the desired indamine salt, which acid salt is more soluble in water than the desired indamine salt, or in an inert solvent such as methylisobutylketone, dioxane or benzene which can also contain an acid corresponding to the desired indamine salt.

When the condensation is performed in water, it is possible, by addition to the reaction mixture of stoichiometric amounts of a salt such as sodium chloride, ammonium persulfate, sodium perchlorate or zinc chloride, to isolate the indamine resulting from this condensation in the form of a salt that is relatively insoluble in water.

When it is desired to prepare indamine salts that are very soluble in water, this condensation is preferably performed in a solvent, as described above. There is then added to the solvent stoichiometric amounts of an acid corresponding to the desired indamine salt. Representative of such acids are, for instance, acetic acid and propionic acid.

Representative benzoquinonediimines of formula (IV) which can be used in this embodiment of the present invention include, for instance, 2-methyl 5-methoxy benzoquinonediimine, 2,5-dimethoxy benzoquinonediimine, 2,6-dimethyl 5-methoxy benzoquinonediimine and durobenzoquinonediimine.

In the embodiment, the condensation reaction is also generally carried out at atmospheric pressure and at a temperature ranging between about −15° C to 50° C. Usually, the benzoquinonediimine and the compound represented by formmula (III) as defined immediately above are employed in essentially equimolar amounts.

In yet another embodiment of the present invention the indamines of formula (I) and their salts can also be prepared by condensing a compound of formula (III) above wherein Y, $Y_3$, $Y_4$ and $Y_5$ have the meaning given above and $Y_1$ and $Y_2$ both represent hydrogen, on a nitroso derivative having the formula:

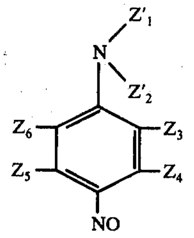

(V)

wherein $Z'_1$ and $Z'_2$ each represent a member selected from the group consisting of lower alkyl having 1–4 carbon atoms and lower alkyl having 1–4 carbon atoms and substituted by a member selected from the group consisting of hydroxy, acylamino wherein the acyl moiety has 1 to 4 carbon atoms, carbamyl, piperidino, benzoylamino and alkylsulfonamido wherein the alkyl moeity has 1 to 4 carbon atoms and $Z_3$, $Z_4$, $Z_5$ and $Z_6$ have the meaning given above. This condensation is carried out either in an aqueous medium, or in an ethanol medium containing zinc chloride. If necessary, the product obtained can be converted into the desired indamine or indamine salt in the manner described hereinbefore.

Preferably the nitroso derivative of formula (V) is used in the form of its hydrobromide or hydrochloride when the condensation reaction is carried out in an aqueous medium. The operating temperature is then between 30° and 50° C and, after cooling, the indamine of formula (I) is isolated in hydrochloride or hydrobromide form which can then be converted into the indamine itself or another of its salts.

When the condensation reaction is effected using the above nitroso derivative of formula (V) in the aforementioned ethanol medium, the operation is carried out at reflux and in the presence of zinc chloride. The resulting indamine of formula (I) is then isolated in the form of its double zinc chloride, which can then be converted into the indamine itself or another of its salts, also in the manner as described heretofore.

Representative nitroso derivatives of formula (V) that can be used in this embodiment of the present invention include, for instance, paranitroso, N,N-diethylaniline, paranitroso-N,N-(ethyl, β-piperidinoethyl) aniline, paranitroso N,N-(ethyl, β-acetylaminoethyl) aniline and paranitroso N,N-(di-β-hydroxyethyl) aniline.

Again, the nitroso derivative defined above and the compound of formula (III) are employed in essentially equimolar amounts. When the reaction medium used is an ethanol medium containing zinc chloride, the latter is used in amounts sufficient for precipitating the product.

The indamines according to the invention, and their salts, constitute dyes which have a great dyeing power in a broad pH range, which can vary from pH 3 to pH 10. Because of their very great affinity for keratinous fibers, very slight concentrations of these dyes are sufficient to obtain intense shades, which explains why those salts thereof which are relatively insoluble in water, such as the persulfates and certain chlorides, are perfectly usable.

Consequently, the present invention also provides novel dye composition for keratinous fibers, in particular, for human hair, characterized by the fact that it contains in solution at least one compound represented by formula (I) or a salt of this compound.

The dye compositions according to the invention can contain only the compounds of formula (I), in which case they make it possible to obtain on white hair colorings which go from violet to green, after an extremely short application period of the order of three minutes at ambient temperature.

Because of the great dyeing power of the novel compounds of formula (I) their concentration in the compositions according to the invention can, as said above, be extremely slight, of the order of 0.002% by weight. However, this concentration can vary from 0.002 to 1% by weight.

The compositions according to the invention can also contain other direct dyes, for example, anthraquinone dyes, nitro dyes of the benzene series, indoanilines, indophenols or indamines other than those of formula (I).

The compositions according to the invention make it possible to obtain shades rich in glints which often give the hair a pearly appearance.

The dye compositions according to the invention are generally in the form of aqueous or aqueous alcohol solutions which can easily be prepared by dissolving in water one or more compounds of formula (I) in mixture or not with other direct dyes. However, they can also contain thickeners and be in the form of creams or gels. When an alcohol solution is employed generally the alcohol will be a lower alkanol such as ethanol or isopropanol, the alkanol being present in the aqueous solution in amounts of about 20 to 70 percent by weight thereof.

The compositions according to the invention can further contain various ingredients usually used in cosmetics, for example, wetting agents, dispersing agents, swelling agents, penetrating agents, softeners or perfumes.

Representative of such materials are nonylphenol oxyethylenated with 4 moles of ethylene oxide, lauryl alcohol oxyethylenated with 10.5 moles of ethylene oxide, a mixture of 19% of dodecyl alcohol oxyethylenated with 2 moles of ethylene oxide and 81% of the sodium sulfate of this same oxyethylenated alcohol, ethanolamides of the fatty acids of coprah which are surface active agents usually employed as wetting agents, carboxymethyl cellulose as a thickening agent, monomethyl ether of ethylene glycol and butyl glycol as solvents and ethylene diamine tetraacetic acid as a sequestering agent.

The compositions of this invention can also be packaged under pressure in aerosol bombs or containers, together with a conventional aerosol propellant such as dichlorodifluoromethane, trichloromonofluoromethane and their mixtures. Obviously other conventional aerosol propellants can be used.

The pH of the dye compositions according to the invention can vary from 3 to 10. Preferably, however, the pH ranges between about 6 – 9.

Dyeing of keratinous fibers, in particular, human hair, with the dye compositions according to the invention, can be performed in the usual way by application of the composition to the fibers to be dyed, the composition being left in contact with the fibers for a time varying from about 3 to 30 minutes. Following this application, the fibers are rinsed and, if desired, washed. Thereafter, the thus treated fibers are dried.

In another embodiment of the present invention, the novel indamines can be employed in the production of capillary hair-setting lotions. These lotions comprise an aqueous alcohol solution, at least a cosmetic resin and at least one compound of formula (I) or a salt thereof. The amount of indamine present in the hair-setting lotion according to this invention can be extremely low. Such an amount generally ranges between about 0.002 to 0.5% by weight of the total hair-setting lotion composition.

Representative cosmetic resins that can be employed in the hair-setting lotion composition of the present invention include, for instance, polyvinylpyrrolidone having a molecular weight of 10,000–70,000, copolymer of crotonic acid and vinyl acetate (10:90) having a molecular weight of 45,000–50,000, copolymer of vinylpyrrolidone and vinyl acetate wherein the ratio of VP to VA ranges between 30–70:70:–30 and having a molecular weight of 40,000 to 160,000 copolymer of maleic anhydride and butylvinyl ether and the like. These resins are utilized in a proportion of about 1 to 3% by weight of the hairsetting lotion composition.

The alcohols suitable for the preparation of the hair-setting lotions of the invention are low molecular weight alkanols, preferably ethanol or isopropanol, which are present in amounts of about 20 to 50% by weight of the total hair-setting lotion composition. The pH of the hair-setting lotion of the invention can vary between 3 - 10 and preferably between about 6–8.

Hair-setting lotions of the present invention that contain only the dyes of formula (I) constitute shading compositions which make it possible to impart to the hair extremely luminous glints and often give it a pearly or iridescent appearance.

However, the hair-setting lotions of this invention can also contain other direct dyes, for example, anthraquinone dyes, nitro dyes of the benzene series, indoanilines, indophenols or again other indamines.

The hair-setting lotions according to the invention are usually used by application to wet hair previously washed and rinsed, followed by rolling up and drying of the hair.

The following examples are intended to illustrate the various aspects of the present invention. Unless otherwise specified, all parts and percentages are by weight and all temperatures are expressed in degrees centigrade.

EXAMPLE 1

The hydrochloride of N-[(4'-dimethylamino)phenyl] 3-amino 6-methoxy benzoquinonediimine is prepared as follows:

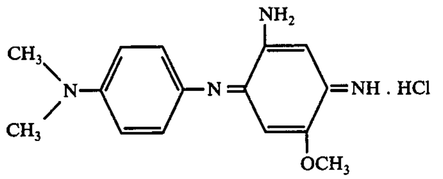

0.171 mole (32 g) of p-nitrosodimethylaniline hydrochloride is dissolved in 320 cc of water at50°. There is then added to this solution, with stirring, 0.171 mole (23.7 g) of 2,4-diamino anisole in 320 cc of water. The reaction medium is allowed to stand for two hours at ambient temperature. Then 41.7 g of chromatographically pure indamine hydrochloride are filtered therefrom, which indamine hydrochloride melts with decomposition at 220°.

EXAMPLE 2

N-[(4'-dimethylamino)phenyl] 3-amino 6-methoxy benzoquinonediimine is prepared as follows:

0.0031 mole (1 g) of the indamine hydrochloride prepared in Example 1 is introduced, with stirring, into 20 cc of water to which have been added 5 cc of ammonia at 22° Be. 0.74 g of the above desired product is filtered therefrom, washed with water and dried under vacuum. This product melts at 205°.

Molecular mass calculated for $C_{15}H_{18}N_4O$ : 270. Molecular mass found by potentiometric determination by perchloric acid in acetic acid: 276.

| Analysis | Calculated for $C_{15}H_{18}N_4O$ | Found | |
|---|---|---|---|
| 0 % | 66.66 | 66.60 | 66.22 |
| H % | 6.66 | 6.83 | 6.76 |
| N % | 20.74 | 20.64 | 20.72 |

EXAMPLE 3

The double chloride of zinc and N-[(4'-[ethyl, acetylaminoethyl]amino)phenyl] 3-amino 6-methoxy benzoquinonediimine having the below formula is prepared as follows:

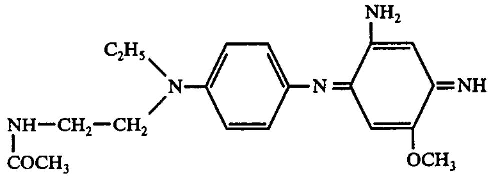

To a solution of 0.01 mole (2.35 g) of paranitroso N,N-(ethyl, β-acetylaminoethyl) aniline in 10 cc of absolute ethanol there are added, on the one hand, 0.01 mole (1.38 g) of 2,4-diamino anisole in solution in 10 cc of absolute ethanol and, on the other hand, 1.36 g of zinc chloride. The reaction medium is heated for a half hour at reflux. Then the above double salt of zinc and indamine which has precipitated in crystallized form (4.2 g) is filtered therefrom. This salt, after washing with ethanol, is chromatographically pure.

EXAMPLE 4

The double chloride of zinc and N-[(4'[ethyl β-piperidinoethyl]amino)phenyl] 3-amino 6-methoxy benzoquinonediimine having the below formula is prepared as follows:

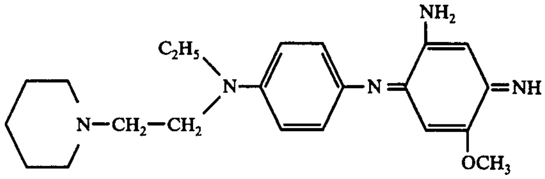

To a solution of 0.01 mole (2.61 g) of paranitroso N,N-(ethyl, β-piperidinoethyl) aniline in 10 cc of absolute ethanol, there are added, on the one hand, 0.01 mole (1.38 g) of 2,4-diamino anisole in solution in 10 cc of absolute ethanol and, on the other hand, 2 g of zinc chloride. The reaction medium is heated for 30 minutes at reflux. The above salt precipitates and is filtered from the reaction medium and washed with boiling ethanol. 4.55 g of chromatography pure double zinc and indamine chloride are thus recovered.

EXAMPLE 5

The persulfate of N-[(4'-dimethylamino)phenyl] 3-acetylamino 6-methyl benzoquinonediimine is prepared as follows:

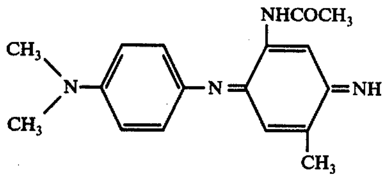

To a solution of 0.03 mole (6.27 g) of N,N-dimethyl paraphenylenediamine dihydrochloride in 20 cc of water to which have been added 20 cc of ammonia at 22° Be there are added, on the one hand, 0.03 mole of 3-amino 4-methyl acetanilide (4.92 g) in solution in 40 cc of acetone and, on the other hand, 50 cc of 50 volume hydrogen peroxide. The reaction mixture is allowed to stand for 10 minutes at ambient temperature. There are added to this reaction mixture 13.7 g of ammonium persulfate in solution in 25 cc of water. The above indamine persulfate precipitates and is filtered from the reaction medium, washed with a little water and then with acetone. 4.5 g of indamine persulfate in the form of green crystals with golden glints are thus recovered in chromatographically pure form.

EXAMPLE 6

N-[(4'-dimethylamino)phenyl] 3-acetylamino 6-methyl benzoquinonediimine is prepared as follows:

There are introduced with stirring, 2 g of the indamine persulfate prepared in Example 5, into 30 cc of water to which have been added 6 cc of ammonia at 22° Be. Stirring is maintained for five minutes. Then the desired indamine (1.1 g) is filtered and washed with water, the resulting indamine melting, after drying under vacuum, at 161°. Molecular mass calculated for $C_{17}H_{20}N_4O$ : 296. Molecular mass found by potentiometric determination by perchloric acid in acetic acid: 287.

| Analysis | Calculated for $C_{17}H_{20}N_4O$ | Found | |
|---|---|---|---|
| C % | 68.91 | 68.24 | 68.37 |
| H % | 6.75 | 6.73 | 6.82 |
| N % | 18.91 | 18.77 | 18.81 |

EXAMPLE 7

The perchlorate of N-[(2'-amino 4'-dimethylamino)-phenyl] benzoquinonediimine is prepared as follows:

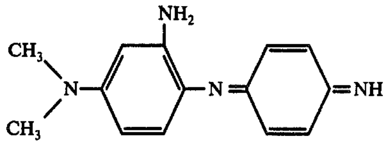

0.01 mole (1 g) of paraphenylenediamine and 0.005 mole (1 g) of N,N-dimethyl metaphenylenediamine dihydrochloride are dissolved in 20 cc of water. To this solution are added 5 cc of ammonia at 22° Be and 20 cc of 20 volume hydrogen peroxide. The resulting reaction mixture, having been allowed to stand for a half hour at ambient temperature is then saturated with sodium perchlorate. After 5 hours at 0°, 0.65 grams of crude indamine perchlorate is filtered therefrom and contains, as its chromatogram shows, N,N-dimethyl metapheneylenediamine and traces of paraphenylenediamine. After washing in ethyl acetate, the product (0.55 g) is chromatographically pure.

EXAMPLE 8

The acetate of N-[(2'-acetylamino-4'-dimethylamino)phenyl] 3-methoxy 6-methyl benzoquinonediimine is prepared as follows:

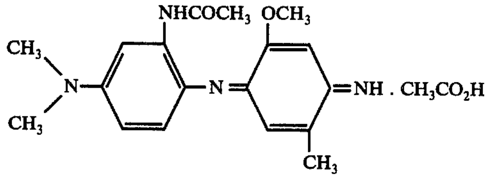

0.05 mole (7.5 g) of 2-methyl 5-methoxy benzoquinonediimine is dissolved in 100 cc of methylisobutylketone. There is then immediately added to this solution 0.05 mole (8.9 g) of meta-(N,N-dimethylamino) acetanilide dissolved in 100 cc of methylisobutylketone to which have been added 5 cc of acetic acid. The above indamine acetate precipitates and is immediately filtered from the reaction medium, washed with a little methylisobutylketone and dried under vacuum. The desired indamine acetate which is in the form of green crystals with golden glints (6 g) is chromatographically pure and melts with decomposition at 133°. Molecular mass calculated for $C_{18}H_{22}O_2N_4CH_3CO_2H$: 386. Molecular mass found by potentiometric determination by perchloric acid in acetic acid: 395.

| Analysis | Calculated for $C_{18}H_{22}O_2N_4CH_3CO_2H$ | Found | |
|---|---|---|---|
| C % | 62.17 | 61.80 | 61.58 |
| H % | 6.73 | 6.57 | 6.60 |
| N % | 14.50 | 14.28 | 14.26 |

EXAMPLE 9

The double chloride of zinc and N-[(4'-diethylamino 2'-hydroxy)phenyl] 3-methoxy 6-methyl benzoquinonediimine having the below formula is prepared as follows:

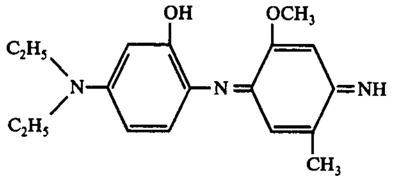

On the one hand, 0.005 mole (1 g) of the hydrochloride of meta-(N,N-diethylamino) phenol is dissolved in 5 cc of water and 10 cc of isopropanol to which have been added 3 cc of ammonia at 22° Be. On the other hand, 0.01 mole (2.25 g) of dihydrochloride of 2-methyl 5-methoxy paraphenylenediamine is dissolved in 10 cc of water and 10 cc of acetone to which have been added 3 cc of ammonia at 22° Be. To this latter solution is immediately added the above solution of meta-(N,N-diethylamino)phenol and 20 cc of 20 volume hydrogen peroxide. The resulting reaction mixture is allowed to stand for 10 minutes at ambient temperature and a small amount of the 2-methyl 5-methoxy paraphenylenediamine is eliminated by filtering. The remaining reaction mixture is then neutralized to a pH of 7 by the addition thereto of acetic acid, and 8 g of zinc chloride in solution in 50 cc of water are also added. After cooling in ice, 2.4 g of the above chromatographically pure double zinc chloride are filtered and recovered.

EXAMPLE 10

The double chloride of zinc and N-[(4'-diethylamino-2'-hydroxy)phenyl] 2,6-dimethyl-3-methoxy benzoquinonediimine having the below formula is prepared as follows:

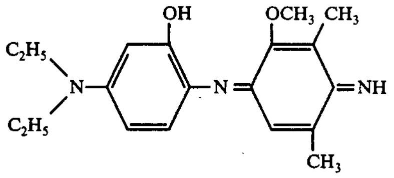

0.005 mole (0.82 g) of 2,6-dimethyl 3-methoxy benzoquinonediimine is dissolved in 6 cc of water. There is immediately added to this solution 0.005 mole (1 g) of meta-(N,N-diethylamino)phenol hydrochloride previously dissolved in 5 cc of water to which have been added 6 cc of isopropyl alcohol and 0.5 cc of ammonia at 22° Be. The resulting mixture immediately takes on an intense blue violet coloring. To this mixture there is then added a solution of 2 g of zinc chloride in 3 cc of water. 1.3 g of the above double chloride of zinc and indamine precipitate and are filtered therefrom and washed with a little water, then with acetone, and finally dried. The product is chromatographically pure.

EXAMPLE 11

The perchlorate of N-[(4'-diethylamino 2'-amino phenyl] 2,6-dimethyl 3-methoxy benzoquinonediimine is prepared as follows:

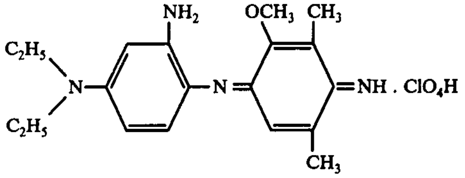

0.01 mole (1.64 g) of 2,6-dimethyl 3-methoxy benzoquinonediimine is dissolved in 6 cc of water. There is immediately added to this solution 0.01 mole (2.4 g) of N,N-diethyl metaphenylenediamine dihydrochloride previously dissolved in 6 cc of water to which have been added 2 cc of ammonia at 22° Be. The resulting mixture immediately takes on an intense blue coloring. To this mixture is added 0.0131 mole (1.6 g) of sodium perchlorate dissolved in 3 cc of water. 0.8 g of the above indamine perchlorate precipitates and is filtered from the reaction mixture. Thereafter the said indamine perchlorate is washed with a little water then with a little dioxane. The product is chromatographically pure.

EXAMPLE 12

The hydrochloride of N-[(4'-diethylamino) phenyl] 3-amino-6-methoxy benzoquinonediimine is prepared as follows:

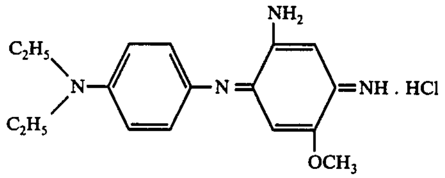

0.1 mole (21.4 g) of p-nitrosodiethylaniline hydrochloride is dissolved in 250 cc of water at 50°. There is then added to this solution, with stirring, 0.1 mole (21.1 g) of 2,4-diamino anisole dihydrochloride in solution in 210 cc of water to which has been added sufficient ammonia at 22° Be to achieve a pH of 8.5. The resulting reaction medium is heated for several minutes at 60°, then left to return slowly to ambient temperature. The precipitate obtained (24.8 g), which is the above indamine hydrochloride, is filtered, washed with a little water and then with acetone. This product is chromatographically pure and melts with decomposition at 180°.

EXAMPLE 13

N-[(4'-diethylamino)phenyl] 3-amino-6-methoxy benzoquinonediimine is prepared as follows:

0.024 mole (7.75 g) of the indamine hydrochloride prepared in Example 12 above, is dissolved in 150 cc of ice water. There is then added to this solution little by little, with stirring, a 4 N soda solution, until total precipitation of the desired indamine occurs. The product is then filtered, carefully washed with water and dried under a vacuum. It melts at 163°.

Molecular mass calculated for $C_{17}H_{22}N_4O$: 298.
Molecular mass found by potentiometric determination by perchloric acid in acetic acid: 296.

| Analysis | Calculated for $C_{17}H_{22}N_40$ | | Found |
|---|---|---|---|
| C % | 68.43 | 68.47 | 68.39 |
| H % | 7.43 | 7.47 | 7.39 |

-continued

| Analysis | Calculated for $C_{17}H_{22}N_4O$ | Found | |
|---|---|---|---|
| N % | 18.78 | 18.89 | 18.64 |

EXAMPLE 14

The persulfate of N-[(4'-N-[ethyl, β-mesylaminoethyl]-amino-2'-methyl)phenyl]-3-acetylamino-6-methyl benzoquinone diimine is prepared as follows:

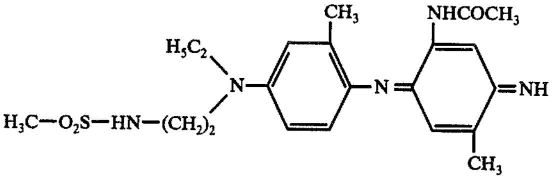

0.0025 mole (0.68 g) of N,N-(ethyl, β-mesylaminoethyl) 4-amino 3-methyl aniline and 0.0025 mole (0.42 g) of 2-methyl 5-acetylamino aniline are dissolved in 10 cc of water to which have been added 10 cc of isopropanol and 1 cc of ammonia at 22° Be. To this resulting solution, cooled to 0°, is added little by little, with stirring, 0.005 mole (1.15 g) of ammonium persulfate in solution in 12 cc of water. The above desired indamine persulfate precipitates and is filtered therefrom and is washed with isopropanol. The product is chromatographically pure.

EXAMPLE 15

The hydrochloride of N-[(4'-dibutylamino)phenyl]-2-methyl-5-amino benzoquinonediimine having the following formula is prepared as follows:

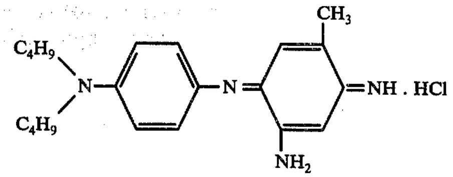

0.01 mole (2.7 g) of hydrochloride of 4-nitroso-N,N-dibutylaniline and 0.01 mole (1.22 g) of 2,4-diamino toluene are introduced into 40 cc of water. The resulting mixture is left to stand for one hour at ambient temperature and then overnight at 0° C. The above indoaniline which crystallizes in the reaction mixture in the form of the hydrochloride thereof is then filtered, washed with water and dried under a vacuum. It melts with decomposition at 146° C.

| Analysis | Calculated for $C_{21}H_{31}N_4Cl$ | Found | |
|---|---|---|---|
| N % | 14.95 | 14.62 | 14.59 |
| Cl % | 9.47 | 9.35 | 9.32 |

N-[(4'-di-β-hydroxyethylamino)phenyl]-2-methoxy-5-amino benzoquinonediimine of the formula

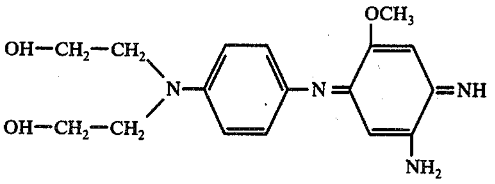

is prepared as follows:

0.02 mole (4.92 g) of 4-nitroso-N,N-di-β-hydroxyethylaniline hydrochloride and 0.02 mole (4.22 g) of 2,4-diamino anisole dihydrochloride are dissolved in 55 cc of a 0.7 N NaOH solution. The resulting solution is maintained for 1.5 hours at ambient temperature with agitation at which time there are added little by little and with cooling, 25 cc of ammonia (22° Be). The above indoaniline precipitates and is filtered, washed with water, recrystallized in a mixture of dimethylformamide and water and dried under vacuum. It melts at 171° C.

| Analysis | Calculated for $C_{17}H_{22}N_4O_3$ | Found | |
|---|---|---|---|
| C % | 61.80 | 61.88 | 62.10 |
| H % | 6.71 | 6.79 | 6.77 |
| N % | 16.96 | 17.14 | 17.04 |

EXAMPLE 17

Monohydrated N-[(4'-(ethyl-carbamylmethyl-)amino)phenyl]-2-methyl-5-amino benzoquinonediimine hydrochloride of the formula:

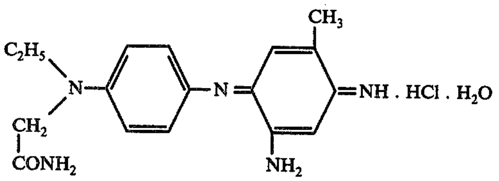

is prepared as follows:

Into 20 cc of a 0.25 N HCl solution there are introduced 0.005 mole (1.03 g) of 4-nitroso-N,N-ethyl-carbamylmethyl aniline and 0.005 mole (0.61 g) of 2,4-diamino toluene. The resulting mixture is left to stand with agitation for 1 hour at ambient temperature. The above monohydrated indamine hydrochloride crystallizes and is then filtered, washed first with ice water and then with acetone and finally dried under a vacuum. It melts with decomposition at 217° C.

| Analysis | Calculated for $C_{17}H_{24}N_5O_2Cl$ | Found | |
|---|---|---|---|
| C % | 55.90 | 55.66 | 55.58 |
| H % | 6.57 | 6.33 | 6.30 |
| N % | 19.15 | 19.02 | 19.24 |
| Cl % | 9.72 | 9.68 | 9.64 |

EXAMPLE 18

Monohydrated N-[4'-(ethyl-carbamylmethyl) amino phenyl]-2-methoxy-5-amino benzoquinonediimine hydrochloride of the formula:

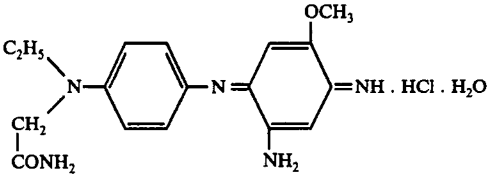

is prepared as follows:

Into 15 cc of isopropanol to which have been added 5 cc of water there are introduced 0.005 mole (1.03 g) of 4-nitroso-N,N-ethyl-carbamylmethyl aniline and 0.005 mole (1.05 g) of 2,4-diamino anisole di-hydrochloride. The resulting mixture is left to stand with agitation for 30 minutes at ambient temperature. The above monohydrated indamine hydrochloride crystallizes and is then filtered, washed first with isopropanol and then with acetone, and recrystallized in boiling water. It melts with decomposition at 214° C.

| Analysis | Calculated for $C_{17}H_{24}N_5O_3Cl$ | Found | |
|---|---|---|---|
| C % | 53.47 | 53.69 | 53.56 |
| H % | 6.27 | 6.33 | 6.35 |
| N % | 18.34 | 17.99 | 18.06 |
| Cl % | 9.31 | 9.31 | 9.41 |

EXAMPLE 19

N-[(4'-(ethyl-β-piperidinoethyl)amino)phenyl]-2-methyl-5-amino benzoquinonediimine hydrochloride of the formula:

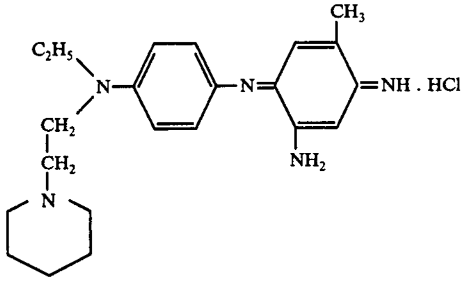

0.005 mole (1.67 g) of 4-nitroso-N,N-(ethyl-β-piperidinoethyl) aniline dihydrochloride and 0.005 mole (0.61 g) of 2,4-diamino toluene are introduced into 20 cc of water. The resulting mixture is maintained with agitation at ambient temperature for one hour at which point there are added 100 cc of water and then sufficient ammonia (22° Be) to adjust the pH thereof to 7.5. The above indoaniline hydrochloride precipitates and is then filtered, washed with a little ice water and dried under a vacuum. It melts with decomposition at 157° C.

| Analysis | Calculated for $C_{22}H_{32}N_5Cl$ | Found | |
|---|---|---|---|
| C % | 65.76 | 65.12 | 65.24 |
| H % | 8.03 | 8.26 | 7.98 |
| N % | 17.44 | 17.36 | 17.23 |
| Cl % | 8.84 | 8.46 | 8.49 |

EXAMPLE 20

Monohydrated N-[(4'-(ethyl-β-piperidinoethyl-)amino)phenyl]-2-methoxy-5-amino benzoquinonediimine hydrochloride of the formula:

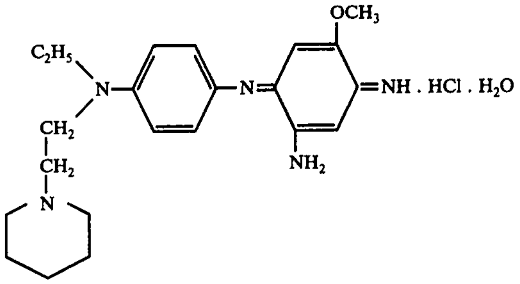

is prepared as follows:

0.01 mole (3.34 g) of 4-nitroso-N,N-(ethyl-β-piperidinoethyl) aniline dihydrochloride and 0.01 mole (2.11 g) of 2,4-diamino anisole dihydrochloride are dissolved in 100 cc of water. The resulting mixture is maintained with agitation for one hour at ambient temperature at which point it is alkalinized, while cooling it to 0° C with agitation by adding thereto sufficient ammonia (22° Be) to adjust its pH to 7.5. The above monohydrated indamine hydrochloride precipitates and is then filtered, washed with a little ice water and then recrystallized in boiling water (10 cc of water per gram of product). After drying under a vacuum the crystallized product melts with decomposition at 120° C.

| Analysis | Calculated for $C_{22}H_{34}N_5Cl\ O_2$ | Found | |
|---|---|---|---|
| C % | 60.60 | 59.98 | 60.12 |
| H % | 7.80 | 7.31 | 7.44 |
| N % | 16.07 | 16.02 | 15.87 |
| Cl % | 8.15 | 7.98 | 7.94 |

EXAMPLE 21

N-[(4'-(ethyl-β-benzoylaminoethyl)amino)phenyl]-2-methoxy-5-amino benzoquinonediimine hydrochloride of the formula:

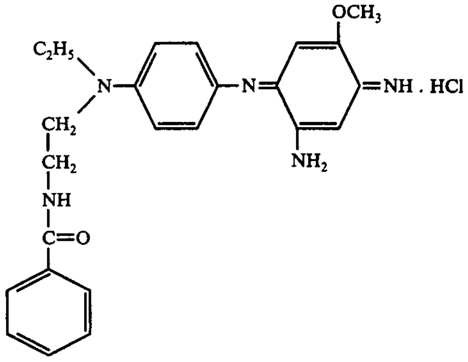

is prepared as follows:

0.02 mole (4.22 g) of 2,4-diamino anisole di-hydrochloride is dissolved in 40 cc of water. The resulting solution is then alkalinized by the addition thereto of sufficient ammonia (22° Be) to adjust the pH thereof to 8.5. There is then introduced, with agitation, 0.02 mole (7 g) of 4-nitroso-N,N-(ethyl-β-benzoylamino ethyl) aniline hydrochloride suspended in 10 cc of isopropanol. The resulting mixture is maintained with agitation at ambient temperature for two hours at which point the above indamine hydrochloride which has crystallized is filtered, washed with ice water and dried under a vacuum. It melts with decomposition at 162° C.

| Analysis | Calculated for $C_{24}H_{28}O_2N_5Cl$ | Found | |
|---|---|---|---|
| N % | 15.43 | 15.17 | 15.25 |
| Cl % | 7.82 | 8.00 | 8.02 |

EXAMPLE 22

N-[(4'-(ethyl-mesylaminoethyl)amino-2'-methyl) phenyl]-2-methyl-5-amino benzoquinonediimine perchlorate of the formula:

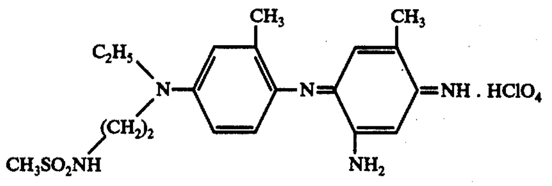

is prepared as follows:

0.02 mole (5.7 g) of 2,4-diamino toluene and 0.02 mole of 4-nitroso-N,N-(ethyl-β-mesylamino ethyl) aniline are dissolved in 40 cc of 0.5N HCl. The resulting mixture is left to stand for three days at ambient temperature at which point there are added 60 cc of water and sufficient potassium perchlorate to precipitate the above indamine in the form of its perchlorate. This precipitate is then filtered, washed with a little ice water and then dried under a vacuum. It melts with decomposition at 107° C and is chromatographically pure.

EXAMPLE 23

The following dye composition is prepared:

| | | |
|---|---|---|
| Dye of Example 1 | 0.1 | g |
| Ethyl alcohol, 96° titer | 20 | g |
| Water, q.s.p. | 100 | g |
| Ammonia at 22° Be, q.s.p. | pH 10 | |

This dye composition when applied to 95% naturally white hair for 10 minutes imparts thereto, after rinsing and shampooing, a very luminous intense blue shading.

EXAMPLE 24

The following hair-setting lotion composition is prepared:

| | | |
|---|---|---|
| Dye of Example 2 | 0.05 | g |
| Vinyl acetate-crotonic acid copolymer (90% vinyl acetate, 10% crotonic acid - molecular weight 45,000) | 2 | g |
| Ethyl alcohol, 96° titer, q.s.p. 50° | | |
| Water, q.s.p. | 100 | g |
| Triethanolamine, q.s.p. | pH 7 | |

This hair-setting lotion when applied to bleached hair imparts thereto a periwinkle blue shade with pearly glints.

EXAMPLE 25

The following hair-setting lotion composition is prepared:

| | | |
|---|---|---|
| Dye of Example 3 | 0.2 | g |
| Vinyl acetate-crotonic acid copolymer (90% vinyl acetate, 10% crotonic acid - molecular weight 45,000) | 2 | g |
| Ethyl alcohol, 96° titer, q.s.p. 50° | | |
| Triethanolamine q.s.p. | pH 7 | |
| Water, q.s.p. | 100 | g |

This hair-setting lotion when applied to bleached hair imparts thereto a strongly silvered light blue shade.

EXAMPLE 26

The following hair-setting lotion is prepared:

| | | |
|---|---|---|
| Dye of Example 4 | 0.05 | g |
| Vinyl acetate-crotonic acid copolymer (90% vinyl acetate, 10% crotonic acid - molecular weight 45,000 | 2 | g |
| Ethyl alcohol, 96° titer, q.s.p. 50° | | |
| Water, q.s.p. | 100 | g |
| Triethanolamine, q.s.p. | pH 7 | |

This hair-setting lotion when applied to bleached hair imparts thereto a very light pearly blue shade.

EXAMPLE 27

The following dye composition is prepared:

| | | |
|---|---|---|
| Dye of Example 5 | 0.1 | g |
| Water, q.s.p. | 100 | g |
| Ammonia at 22° Be, q.s.p. | pH 9.5 | |

This dye composition when applied to 95% naturally white hair for 20 minutes imparts thereto after rinsing and shampooing, an iridescent blue green shade.

EXAMPLE 28

The following hair-setting lotion composition is prepared:

| | | |
|---|---|---|
| Dye of Example 6 | 0.1 | g |
| Vinyl acetate-crotonic acid copolymer (90% vinyl acetate, 10% crotonic acid - molecular weight 45,000) | 2 | g |
| Isopropyl alcohol, 96° titer, q.s.p. 50° | | |
| Water, q.s.p. | 100 | g |
| Triethanolamine, q.s.p. | pH 7 | |

This hair-setting lotion when applied to bleached hair imparts thereto an intense emerald green shade.

EXAMPLE 29

The following dye composition is prepared:

| | | |
|---|---|---|
| Dye of Example 6 | 0.1 | g |
| Ethyl alcohol, 96° titer | 50 | g |
| Water, q.s.p. | 100 | g |
| Water, q.s.p. | 100 | g |

This dye composition, the pH of which is 8.5, is applied to 95% naturally white hair for 20 minutes. After rinsing and shampooing, a light pearly green shade is obtained.

EXAMPLE 30

The following hair-setting lotion composition is prepared:

| | |
|---|---|
| Dye of Example 7 | 0.025 g |
| Vinyl acetate-crotonic acid copolymer (90% vinyl acetate, 10% crotonic acid - molecular weight 45,000) | 2 g |
| Ethyl alcohol, 96° titer, q.s.p. 50° | |
| Water, q.s.p. | 100 g |
| Triethanolamine, q.s.p. | pH 7 |

This hair-setting lotion when applied to bleached hair imparts thereto a forget-me-not blue shade.

EXAMPLE 31

The following dye composition solution is prepared:

| | |
|---|---|
| Dye of Example 8 | 0.1 g |
| N-[4'-amino 2'-methoxy 3',5'-dimethyl)phenyl] 3-amino 2,6-dimethyl benzoquinone diimine acetate | 0.1 g |
| N-[2',4'-diamino, 5'-methoxy) phenyl] benzoquinoneimine | 0.05 g |
| Water, q.s.p. | 100 g |

The dye composition when applied to bleached hair for 10 minutes imparts thereto, after rinsing and shampooing, a very intense violet shade.

EXAMPLE 32

The following dye composition is prepared:

| | |
|---|---|
| Dye of Example 7 | 0.1 g |
| Ethyl alcohol, 96° titer | 20 g |
| Water, q.s.p. | 100 g |
| 1% lactic acid solution, q.s.p. | pH 3 |

This dye composition when applied to 95% naturally white hair for 20 minutes imparts thereto, after rinsing and shampooing, a rather intense blue gray shade.

EXAMPLE 33

The following hair-setting lotion composition is prepared:

| | |
|---|---|
| Dye of Example 1 | 0.005 g |
| Vinyl acetate-crotonic acid copolymer (90% vinyl acetate, 10% crotonic acid - molecular weight 45,000) | 2 g |
| Ethyl alcohol, 96° titer, q.s.p. 50° | |
| Water, q.s.p. | 100 g |
| Triethanolamine, q.s.p. | pH 7 |

This hair-setting lotion when applied to bleached hair imparts thereto a bluish silver shade.

EXAMPLE 34

The following dye composition is prepared:

| | |
|---|---|
| Dye of Example 2 | 0.025 g |
| Nitroorthophenylenediamine | 0.1 g |
| Ethyl alcohol, 96° titer | 20 g |
| Water, q.s.p. | 100 g |
| Ammonia at 22° Be, q.s.p. | pH 9 |

This dye composition when applied to 95% naturally white hair for 10 minutes imparts thereto, after rinsing and shampoing, a deep intense green shade.

EXAMPLE 35

The following dye composition is prepared:

| | |
|---|---|
| Dye of Example 2 | 0.002 g |
| Ethyl alcohol, 96° titer | 20 g |
| Water, q.s.p. | 100 g |

This dye composition, the pH of which is equal to 9, is applied to 95% naturally white hair for 10 minutes. After rinsing and shampooing, a very light pearly turquoise shade is obtained.

EXAMPLE 36

The following hair-setting lotion composition is prepared:

| | |
|---|---|
| Dye of Example 3 | 0.1 g |
| N-[(2',4'-diamino 5'-methoxy) phenyl] benzoquinoneimine | 0.05 g |
| Vinyl acetate-crotonic acid copolymer (90% vinyl acetate, 10% crotonic acid - molecular weight 45,000) | 2 g |
| Ethyl alcohol, 96° titer, q.s.p. 50° | |
| Water, q.s.p. | 100 g |
| Triethanolamine, q.s.p. | pH 7 |

This hair-setting lotion when applied to bleached hair imparts thereto a silver gray blue shade.

EXAMPLE 37

The following dye composition is prepared:

| | |
|---|---|
| Dye of Example 4 | 0.05 g |
| N-[(4'-hydroxy 3',5'-dimethyl) phenyl] 2,6-dimethyl benzoquinoneimine | 0.1 g |
| Ethyl alcohol, 96° titer | 50 g |
| Water, q.s.p. | 100 g |
| Ammonia at 22° Be, q.s.p. | pH 10 |

This dye composition when applied to 95% naturally white hair for 20 minutes imparts thereto, after rinsing and shampooing, a very brilliant silver gray shade.

EXAMPLE 38

The following dye composition is prepared:

| | |
|---|---|
| Dye of Example 6 | 0.0025 g |
| N-[(4'-hydroxy)phenyl] 3-amino 6-methyl benzoquinoneimine | 0.1 g |
| Ethyl alcohol, 96° titer | 25 g |
| Water, q.s.p. | 100 g |

This dye composition, the pH of which is equal to 9, is applied to bleached hair for 10 minutes. After rinsing and shampooing, a very pale green shade with golden glints is obtained.

EXAMPLE 39

The following dye composition is prepared:

| | |
|---|---|
| Dye of Example 9 | 0.05 g |
| Ethyl alcohol, 96° titer | 20 g |
| Water, q.s.p. | 100 g |
| Ammonia at 22° Be, q.s.p. | pH 10 |

This dye composition when applied to 95% naturally white hair for 3 minutes imparts thereto, after rinsing and shampooing, an intense blue green shade.

EXAMPLE 40

The following dye composition is prepared:

| | | |
|---|---|---|
| Dye of Example 10 | 0.01 | g |
| Ethyl alcohol, 96° titer | 50 | g |
| Water, q.s.p. | 100 | g |

This dye composition, which has a pH of 8, is applied to bleached hair for 10 minutes. After rinsing and shampooing a clear pearly green shade is obtained.

EXAMPLE 41

The following dye composition is prepared:

| | | |
|---|---|---|
| Dye of Example 11 | 0.05 | g |
| Ethyl alcohol, 96° titer | 25 | g |
| Water, q.s.p. | 100 | g |

This dye composition, the pH of which is equal to 8, is applied to 95% naturally white hair for 3 minutes. After rinsing and shampooing, a strongly silvered pale blue green shade is obtained.

EXAMPLE 42

The following hair-setting lotion composition is prepared:

| | | |
|---|---|---|
| Dye of Example 14 | 0.05 | g |
| Vinyl acetate-crotonic acid copolymer (same as in Example 24) | 2 | g |
| Ethyl alcohol, 96° titer | 50 | g |
| Water, q.s.p. | 100 | g |
| Triethanolamine, q.s.p. | pH 7 | |

This hair-setting lotion when applied to bleached hair imparts thereto a pearly light green shade.

EXAMPLE 43

The following dye composition is prepared:

| | | |
|---|---|---|
| Dye of Example 12 | 0.1 | g |
| Water, q.s.p. | 100 | g |
| Ammonia at 22° Be, q.s.p. | pH 10 | |

This dye composition when applied for 15 minutes to 95% naturally white hair imparts thereto, after rinsing and shampooing, a very intense king's blue shade.

EXAMPLE 44

The following hair-setting lotion composition is prepared:

| | | |
|---|---|---|
| Dye of Example 13 | 0.025 | g |
| Vinyl acetate-crotonic acid copolymer (same as in Example 24) | 2 | g |
| Ethyl alcohol 96° titer | 50 | g |
| Water, q.s.p. | 100 | g |
| Triethanolamine, q.s.p. | pH 7 | |

This hair-setting lotion when applied to bleached hair imparts thereto pearly light blue shade.

EXAMPLE 45

The following hair dye composition is prepared:

| | | |
|---|---|---|
| Dye of Example 15 | 0.25 | g |
| Diethanolamides of fatty acids of coprah | 5 | g |
| Ammonia (22° Be) q.s.p. | pH 10 | |
| Water, q.s.p. | 100 | g |

This dye composition when applied for 25 minutes at ambient temperature to 95% naturally white hair imparts thereto, after rinsing and shampooing, a pearly light emerald green coloration.

EXAMPLE 46

The following hair dye composition is prepared:

| | | |
|---|---|---|
| Dye of Example 19 | 0.1 | g |
| Carboxymethyl cellulose | 4 | g |
| Monomethyl ether of ethylene glycol (methyl cellosolve) | 16 | g |
| Ammonia (22° Be) q.s.p. | pH 6.5 | |
| Water, q.s.p. | 100 | g |

This dye composition when applied for 25 minutes at ambient temperature to 95% naturally white hair, after rinsing and shampooing, imparts thereto a very silvery light blue coloration.

EXAMPLE 47

The following dye composition is prepared:

| | | |
|---|---|---|
| Dye of Example 17 | 0.08 | g |
| Nonylphenol oxyethylenated with 4 moles of ethylene oxide | 7 | g |
| Water, q.s.p. | 100 | g |
| Ammonia (22° Be), q.s.p. | pH 10 | |

This dye composition when applied for 20 minutes at ambient temperature to 95% naturally white hair imparts thereto, after rinsing and shampooing a gentian blue coloration.

EXAMPLE 48

The following dye composition is prepared:

| | | |
|---|---|---|
| Dye of Example 20 | 0.15 | g |
| Butylglycol | 5 | g |
| Lauryl alcohol oxyethylenated with 10.5 moles of ethylene oxide | 5 | g |
| Ammonia (22° Be), q.s.p. | pH 7 | |
| Water, q.s.p. | 100 | g |

This dye composition when applied for 20 minutes at ambient temperature to 95% naturally white hair imparts thereto, after rinsing and shampooing, a lavender blue coloration.

EXAMPLE 49

The following hair-setting lotion composition is prepared:

| | | |
|---|---|---|
| Dye of Example 18 | 0.09 | g |
| Polyvinylpyrrolidone (MW = 40,000) | 2 | g |
| Isopropyl alcohol | 35 | g |
| Ammonia (22° Be), q.s.p. | pH 10 | |
| Water, q.s.p. | 100 | g |

This hair setting lotion when applied to bleached hair imparts theretu a very rich royal blue coloration.

EXAMPLE 50

The following dye composition is prepared:

| | |
|---|---|
| Dye of Example 16 | 0.2 g |
| Diethanolamides of fatty acids of coprah | 10 g |
| Lactic acid (5% solution) q.s.p. | pH 7 |
| Water, q.s.p. | 100 g |

This dye composition when applied for 20 minutes at ambient temperature to 95% naturally white hair imparts thereto, after rinsing and shampooing, a horizon blue coloration.

EXAMPLE 51

The following dye composition is prepared:

| | |
|---|---|
| Dye of Example 21 | 1.3 g |
| Butylglycol | 5 g |
| Lauryl alcohol oxyethylenated with 10.5 moles of ethylene oxide | 5 g |
| Water, q.s.p. | 100 g |
| Ammonia (22° Be) q.s.p. | pH 6.5 |

This dye composition when applied for 15 minutes at ambient temperature to 95% naturally white hair imparts thereto a pure blue coloration.

EXAMPLE 52

The following dye composition is prepared:

| | |
|---|---|
| Dye of Example 22 | 0.25 g |
| Mixture of 19% dodecylalcohol oxyethylenated with 2 moles of ethylene oxide and 81% of the sodium sulfate salt of this same oxyethylenated alcohol | 16 g |
| Ethylenediamine tetraacetic acid | 1.5 g |
| Ethanol, 95° titer | 25 g |
| Ammonia (22° Be) q.s.p. | pH 8.5 |
| Water, q.s.p. | 100 g |

This dye composition when applied for 20 minutes at ambient temperature to 95% naturally white hair imparts thereto a pearly light emerald green coloration.

What is claimed is:

1. A double salt of zinc chloride and an indamine having the formula

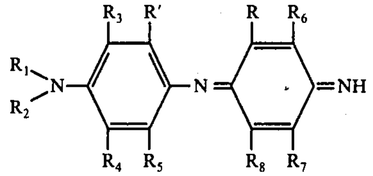

wherein R and R' each independently represent a member selected from the group consisting of hydrogen, lower alkyl having 1-4 carbon atoms, lower alkoxy having 1-4 carbon atoms, amino, acetylamino and hydroxy with the proviso that one, but not both of R and R' is said amino, acetylamino or hydroxy; $R_1$ and $R_2$ each independently represent a member selected from the group consisting of lower alkyl having 1-4 carbon atoms and lower alkyl having 1-4 carbon atoms and substituted with a member selected from the group consisting of hydroxy, acetylamino, carbamyl, benzoylamino and alkyl sulfonamido wherein the alkyl moiety has 1-4 carbon atoms, and $R_3$, $R_4$, $R_5$, $R_6$, $R_7$ and $R_8$ each independently represent a member selected from the group consisting of hydrogen, lower alkyl having 1-4 carbon atoms and lower alkoxy having 1-4 carbon atoms.

* * * * *